(12) United States Patent
Claus et al.

(10) Patent No.: US 8,768,251 B2
(45) Date of Patent: Jul. 1, 2014

(54) EXCLUSIVE PAIRING TECHNIQUE FOR BLUETOOTH COMPLIANT MEDICAL DEVICES

(75) Inventors: Michael J. Claus, Newport Coast, CA (US); Timothy Hunter, Irvine, CA (US); Dung Ma, Westminster, CA (US); Fred Lee, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1159 days.

(21) Appl. No.: 11/750,289

(22) Filed: May 17, 2007

(65) Prior Publication Data

US 2008/0285626 A1    Nov. 20, 2008

(51) Int. Cl.
*H04B 7/00* (2006.01)
(52) U.S. Cl.
USPC .......................... 455/41.2; 455/41.1; 375/133
(58) Field of Classification Search
USPC .......................... 455/41.1, 41.2, 41.3; 375/133
See application file for complete search history.

(56) References Cited

U.S. PATENT DOCUMENTS

| | | | |
|---|---|---|---|
| 5,483,518 A * | 1/1996 | Whetsel | 370/241 |
| 6,886,095 B1 | 4/2005 | Hind et al. | |
| 7,254,159 B1 | 8/2007 | Lavelle et al. | |
| 2002/0197956 A1 | 12/2002 | Annola et al. | |
| 2003/0021262 A1* | 1/2003 | Ma et al. | 370/352 |
| 2003/0065536 A1* | 4/2003 | Hansen et al. | 705/2 |
| 2003/0110929 A1* | 6/2003 | Riopelle | 84/615 |
| 2005/0202852 A1 | 9/2005 | Wada | |
| 2005/0240377 A1* | 10/2005 | Bibelhausen et al. | 702/188 |
| 2006/0031378 A1 | 2/2006 | Vallapureddy et al. | |
| 2006/0128305 A1 | 6/2006 | Delalat | |
| 2006/0135064 A1* | 6/2006 | Cho et al. | 455/41.1 |
| 2007/0173227 A1 | 7/2007 | Brink et al. | |
| 2007/0287418 A1 | 12/2007 | Reddy | |
| 2008/0059239 A1* | 3/2008 | Gerst et al. | 705/3 |
| 2008/0102793 A1 | 5/2008 | Ananthanarayanan et al. | |
| 2008/0220718 A1 | 9/2008 | Sakamoto et al. | |
| 2008/0287062 A1 | 11/2008 | Claus et al. | |

OTHER PUBLICATIONS

Tim Moors et al; "Using short-range communication to control mobile device functionality"; Personal and Ubiquitous Computing, Springer Verlag, LO; vol. 12, No. 1 Nov. 14, 2006; pp. 11-14.
Gehrmann C: "Bluetooth Security White Paper, Bluetooth SIG", Bluetooth Doc, XX, XX, Apr. 19, 2002, pp. 1-46, XP003010085.
International Search Report for Application No. PCT/US08/063554, mailed on Oct. 6, 2008, 3 pages.
International Preliminary Report on Patentability and Written Opinion for Application No. PCT/US08/063554, mailed on Nov. 17, 2009, 7 pages.

* cited by examiner

*Primary Examiner* — Hsin-Chun Liao
(74) *Attorney, Agent, or Firm* — Abbott Medical Optics Inc.

(57) ABSTRACT

A method and system of establishing communications between at least two independent software modules in a safety critical system, such as a medical system, is provided. The design comprises providing an exclusive Bluetooth connection between at least two wireless devices. A master wireless device is configured with Bluetooth master device functionality and a slave wireless device is configured with Bluetooth slave device functionality. The wireless devices are employed in performing a medical procedure. The method further comprises acquiring a stored unique address from the slave wireless device over the Bluetooth connection, comparing the stored unique address to a master wireless device unique address available at the master wireless device, and exclusively pairing the master wireless device and the slave wireless device when the unique address acquired from the slave wireless device is found to identically match the master wireless device unique address.

21 Claims, 10 Drawing Sheets

EXCLUSIVE PAIRING TECHNIQUE FOR BLUETOOTH COMPLIANT MEDICAL DEVICES

BACKGROUND OF THE INVENTION

1. Field of the Invention

The present invention relates generally to the art of medical systems, and more specifically to managing data communications between multiple independent subsystems forming a safety critical system.

2. Description of the Related Art

Today's safety critical systems, such as automated medical system products or surgical equipment, may be constructed as a collection of independent components realized in hardware and software. Constructing a suite of independent components or modules affords medical system product designers and manufacturers the ability to create and deploy subsystems that perform specific functions that are a subset of the complete device or system.

Designs that take advantage of allocating functions to a plurality of specialized subsystems must include a communications mechanism to enable the subsystems to interact. Subsystems may share or communicate control and status information between each other to realize complete system functionality. These communications are typically implemented using a communications protocol that specifies a uniform or consensus format that the subsystems use to transmit and receive information to each other.

Traditionally, medical system products transmit control and status signals between subsystems over a fixed wire or cable using a standard cable interface, such as Universal Serial Bus, Ethernet, etc. Recent developments have made it highly desirable for subsystems to communicate over a wireless network, thus reducing or eliminating the need to use fixed wire cables or backplanes to connect subsystems.

Current wireless implementations based on the Bluetooth™ communications protocol can become unsuitable for interconnection of subsystems forming medical products that typically are interconnected using a fixed wire cable.

A major problem that may result in a hazardous situation when implementing the above-mentioned wireless Bluetooth communications protocol in a medical environment is a slave device subsystem. Such a slave device subsystem in a medical application may include a remote control mechanism or a foot pedal that may mistakenly connect to and unintentionally interact with a foreign or separate master instrument host subsystem. For example, a wireless foot pedal in operating theater A may pair and connect to instrument host A while a surgeon uses the foot pedal during the procedure to control instrument host A. During the conduct of this procedure, another surgeon activates wireless foot pedal in operating theater B and initiates the Bluetooth 'pairing' process. The wireless foot pedal in operating theater B pairs and connects to instrument host B and a surgeon uses the foot pedal during the procedure to control instrument host B.

However, a slave device, i.e. foot pedal, may pair with multiple master devices, i.e. instrument hosts, in a Bluetooth environment. In the foregoing example, the wireless foot pedal in operating theater B also pairs and connects with instrument host A. In this situation, the surgeon in operating theater B is controlling instrument hosts A and B simultaneously while the surgeon in operating theater A is also controlling instrument host A. The simultaneous operation of an instrument host from two wireless foot pedals can create confusion, disrupt a delicate operating procedure, and can potentially cause injury or even death to the patient in operating theater A. The surgeon in operating theater B may successfully control instrument host B in an effort to perform a procedure while unaware that he is simultaneously sending the same control input or signals to instrument host A. The surgeon in operating theater A may observe this interference, but remains unable to address the situation other than to discontinue the procedure, being forced to shut down instrument host A.

Overall system integrity is paramount to designing and deploying safety critical systems. Thus, today's designers are faced with a difficult and complex implementation challenge to ensure wireless communications between desired subsystems provide the required level of safety in an operating theater environment.

Furthermore, the communications protocol employed in the construction of safety critical systems must provide the ability for a slave device to exclusively pair and connect with a pre-selected master device ensuring the slave device is only communicating with a single master device at any given time.

Based on the foregoing, it would be advantageous to provide a wireless connection for use in safety critical systems that overcome the foregoing drawbacks present in previously known Bluetooth communications protocol designs used in the design of medical systems.

SUMMARY OF THE INVENTION

According to one aspect of the present design, there is provided a method and system of establishing communications between at least two independent software modules in a safety critical system, such as a medical system, is provided. The design comprises providing an exclusive Bluetooth connection between at least two wireless devices. A master wireless device is configured with Bluetooth master device functionality and a slave wireless device is configured with Bluetooth slave device functionality. The wireless devices are employed in performing a medical procedure. The method further comprises acquiring a stored unique address from the slave wireless device over the Bluetooth connection, comparing the stored unique address to a master wireless device unique address available at the master wireless device, and exclusively pairing the master wireless device and the slave wireless device when the unique address acquired from the slave wireless device is found to identically match the master wireless device unique address.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for managing Bluetooth data communications between multiple independent subsystems in a safety critical system. The present design may provide a wireless communications protocol for sending and receiving arbitrary data between two subsystems exclusively and ensuring data integrity. The subsystems may perform specific functions that are a sub-set of the complete device or system. With the data communications provided by the present design, the subsystems may perform as two independent software entities. Each software entity may provide the applications and the appropriate underlying operating systems software. The present designs wireless communications protocol may enable exclusive communications to be established between two pre-selected subsystems. The present design may provide an exclusive pairing, sometimes referred to as linking or bonding, mechanism for wireless Bluetooth communications that enables a single slave device to connect and communicate with a single pre-selected master device. Exclusively paired wireless devices may associate with each other and exchange data.

The present design is directed to managing an accurate, reliable, and exclusive communications arrangement for transmitting and receiving data over a wireless Bluetooth communications network between independent subsystems in a system such as a safety critical system.

While the present design may be used in various environments and applications, it will be discussed herein with a particular emphasis on a medical or hospital environment, where a surgeon or health care practitioner performs. For example, embodiments of the present design may include a phacoemulsification surgical system, vitrectomy system, or combined phaco-vitrectomy system comprising an independent graphical user interface (GUI) module, an instrument host module, and a controller module, such as a foot pedal or switch, to control the surgical system.

Figure 1:
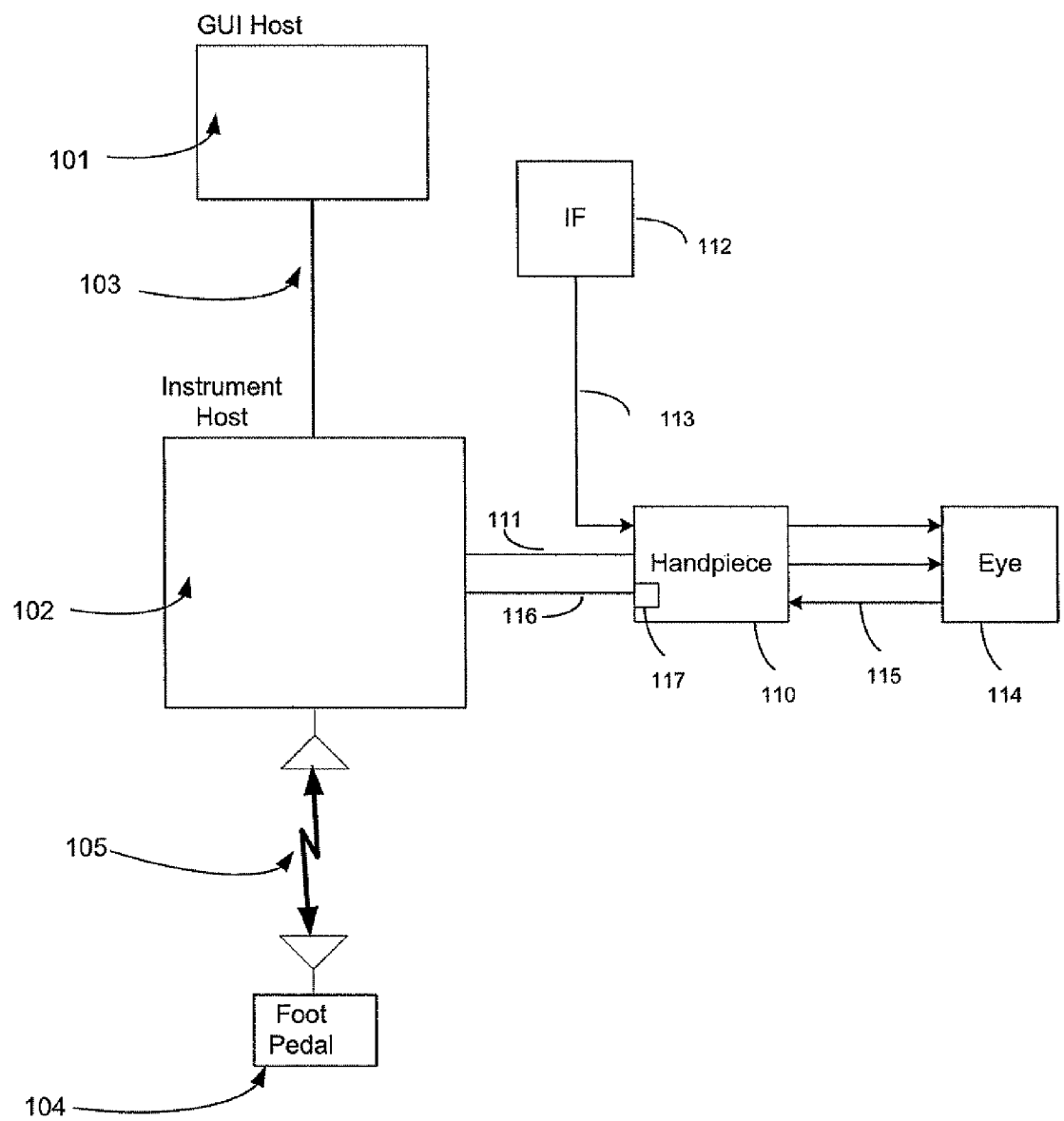
FIG. 1 is a block diagram illustrating the components and interfaces of an exemplary medical system employing the novel communications protocol of the present design.

FIG. 1 illustrates a phacoemulsification system in block diagram form to show the components and interfaces for a safety critical medical system in accordance with the present design. The particular embodiment illustrated in FIG. 1X contemplates that the GUI host 101 subsystem and instrument host 102 subsystem are connected by a serial communication cable 103 for the purposes of controlling the surgical instrument host 102 by the GUI host 101. A wireless footpedal 104 switch subsystem may transmit control signals relating internal physical and virtual switch position information as input to the instrument host 102 over wireless communications network 105.

The phacoemulsification system has a handpiece/needle 110 that includes a needle and electrical means, typically a piezoelectric crystal, for ultrasonically vibrating the needle. The instrument host 102 supplies power on line 111 to a phacoemulsification handpiece/needle 110. An irrigation fluid source 112 is fluidly coupled to handpiece/needle 110 through line 113. The irrigation fluid and ultrasonic power are applied by handpiece/needle 110 to a patient's eye, or affected area or region, indicated diagrammatically by block 114. Alternatively, the irrigation source may be routed to the eye 114 through a separate pathway independent of the handpiece. The eye 114 is aspirated by the instrument host 102 peristaltic pump (not shown) through line/handpiece needle 115 and line 116. A switch 117 disposed on the handpiece 110 may be utilized as a means for enabling a surgeon/operator to select an amplitude of electrical pulses to the handpiece via the instrument host and GUI host. Any suitable input means, such as, for example, a wireless foot pedal 104 switch subsystem may be utilized in lieu of the switch 117.

In FIG. 1, the wireless foot pedal 104 switch subsystem and instrument host 102 may be two separate independent software execution environments comprising the medical system applications software and the underlying operating systems. The present design may provide control and feedback of the medical system by exchanging data between wireless foot pedal 104 switch subsystem and the instrument host 102, between software subsystems within the instrument host, between the instrument host and subsystems external to the instrument host 102 and/or GUI host 101, or between subsystems external to the instrument host 102 and/or GUI host 101. The present design may realize this data exchange using a software algorithm executing in each applicable master and slave device that provides the same lightweight or bandwidth efficient Bluetooth connection configured in an exclusive master-slave data communications relationship. The communications protocol may be implemented in both the wireless foot pedal 104 switch subsystem and instrument host 102 subsystem and arranged to enable either module to act as the master and the other as the slave subsystem as appropriate. More than one software subsystem may employ the protocol and aspects described herein, possibly using different security measures that prohibit synchronizing between remote or unintended slave devices.

Although the particular embodiment illustrated in FIG. 1 contemplates that the GUI host 101 subsystem and instrument host 102 subsystem are connected by a serial communication cable 103, these two host subsystem may also implement the present designs exclusive master-slave data communications relationship. A serial communication cable 103 connection is illustrated in FIG. 1 for simplicity.

Bluetooth Standard

Bluetooth technology provides a communication protocol for use across a short-range radio network. In summary, Bluetooth technology enables communication between two wireless devices without use of a fixed cable connection. The Bluetooth specification addresses the establishment of a communications path to form a wireless connection for the transmission and reception of data, control signals and information across a single communications path.

A Bluetooth device is essentially a cable replacement system that consists of a master and a slave. The Bluetooth communications protocol requires the master and slave devices to first identify themselves to each other. This Bluetooth process is know as 'pairing' and should be well understood by those skilled in the art.

Designs implementing wireless connections using Ericsson's Bluetooth protocol specification have become commonplace in the consumer market. The Bluetooth communications protocol is well suited for replacing a fixed wired cable found in today's consumer products such as a cellular phone to connect the headset, a personal digital assistant to connect and synchronize with other devices.

Implementing the Bluetooth specification yields a communications path between wireless non-fixed devices and subsystems. The Bluetooth specification also addresses providing an interference resistant communications path with automatic error detection and correction capabilities for transmitting and receiving of control signals, data, and information.

The Bluetooth communications protocol enables a slave device pairing with multiple master devices and enables the master device to pair with multiple slave devices. Products implementing Bluetooth communications, establish connectivity between each slave device and its associated masters simultaneously.

Before they can exchange data, Bluetooth implementations employ a pairing process to establish a new relationship between two Bluetooth enabled devices. In this context, "pairing" refers to a mechanism where the two devices exchange protected passkeys and form a link. Once paired, all data and information transmitted over this Bluetooth link are encrypted and only slave devices authorized during the pairing process become able to receive and decipher this encrypted transmission. The Bluetooth specification defines three security modes ranging from requiring no encryption or authentication to requiring encryption with authentication. The present design may operate and function with each Bluetooth security mode.

The operation of today's current state of design for Bluetooth connection establishment will be described in the paragraphs that follow. The teachings are intended to provide a basic foundation for Bluetooth pairing using over-the-air techniques. This basic foundation will form the framework for describing the present design system and method.

In order to establish a connection between a master and slave device in a Bluetooth compliant system, the master device initiates a device pairing process. The pairing process consists of a searching phase and a pairing phase. The searching phase, initiated by the Bluetooth master device, is used to discover all available Bluetooth slave devices. During the searching phase, each slave device responds with its unique address. The Bluetooth master device reports and stores the received addresses. If the intended slave device is not found, the searching process is repeated. After the searching phase concludes, the Bluetooth master device initiates the pairing phase. The pairing phase is used to establish an authentication mechanism between the master and slave device. Successful completion of the pairing phase results in a communication path being established between these two Bluetooth enabled devices.

The pairing process is suitable in a variety of applications and environments. For example, a cellular phone handset may act as a Bluetooth master device and initiate the pairing process with an integrated earpiece and microphone Bluetooth slave device to establish a wireless communication path enabling wireless bi-directional transfer of data and information. In this environment, the searching phase can be achieved in a very short amount of time since there are a limited number of devices available for the cellular phone handset to search.

Figure 2:
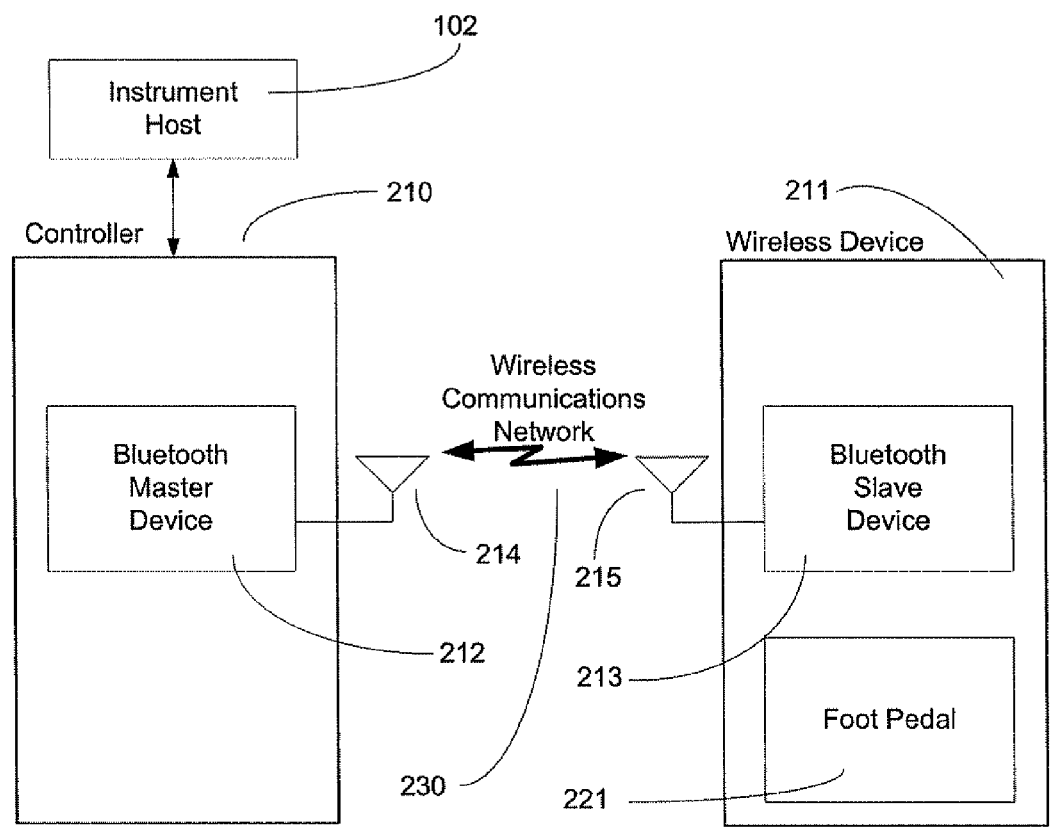
FIG. 2 illustrates the Bluetooth pairing mechanism components, interfaces for searching and pairing master and slave Bluetooth enabled devices.

FIG. 2 illustrates an exemplary communication system employing Bluetooth technology providing a communications path across wireless communications network 230 between antenna 214 connected to controller 210 and antenna 215 connected to wireless device 211. For purposes of illustration, an instrument host 102 manages the wireless controller 210, and the wireless device 211 provides a footpedal 221 used in controlling the instrument host 102. The communication system facilitates bi-directional communication between the instrument host 102 and footpedal 221. The Bluetooth technology is realized by employing a Bluetooth master device 212 and a Bluetooth slave device 213, wherein the Bluetooth master device 212 and the Bluetooth slave device 213 access the wireless communications network 230 to form a communications path between antennas 214 and 215 respectively.

Bluetooth employs a pairing process to establish a new relationship between two Bluetooth enabled devices before they can exchange data. In this context, pairing refers to a mechanism where the two devices are exchanging protected passkeys and form a link. Pairing may be described in terms of a discovery and authentication mechanism. Once paired, all data and information transmitted over this Bluetooth link is encrypted and only those slave devices authorized during the pairing process will be able to receive and decipher this encrypted transmission.

In order to establish a connection between a master and slave device in a Bluetooth compliant system, the master device initiates a device pairing process. The master device searches for one or more slave devices, and then pairs with the slave devices to accomplish the pairing process.

Figure 3:
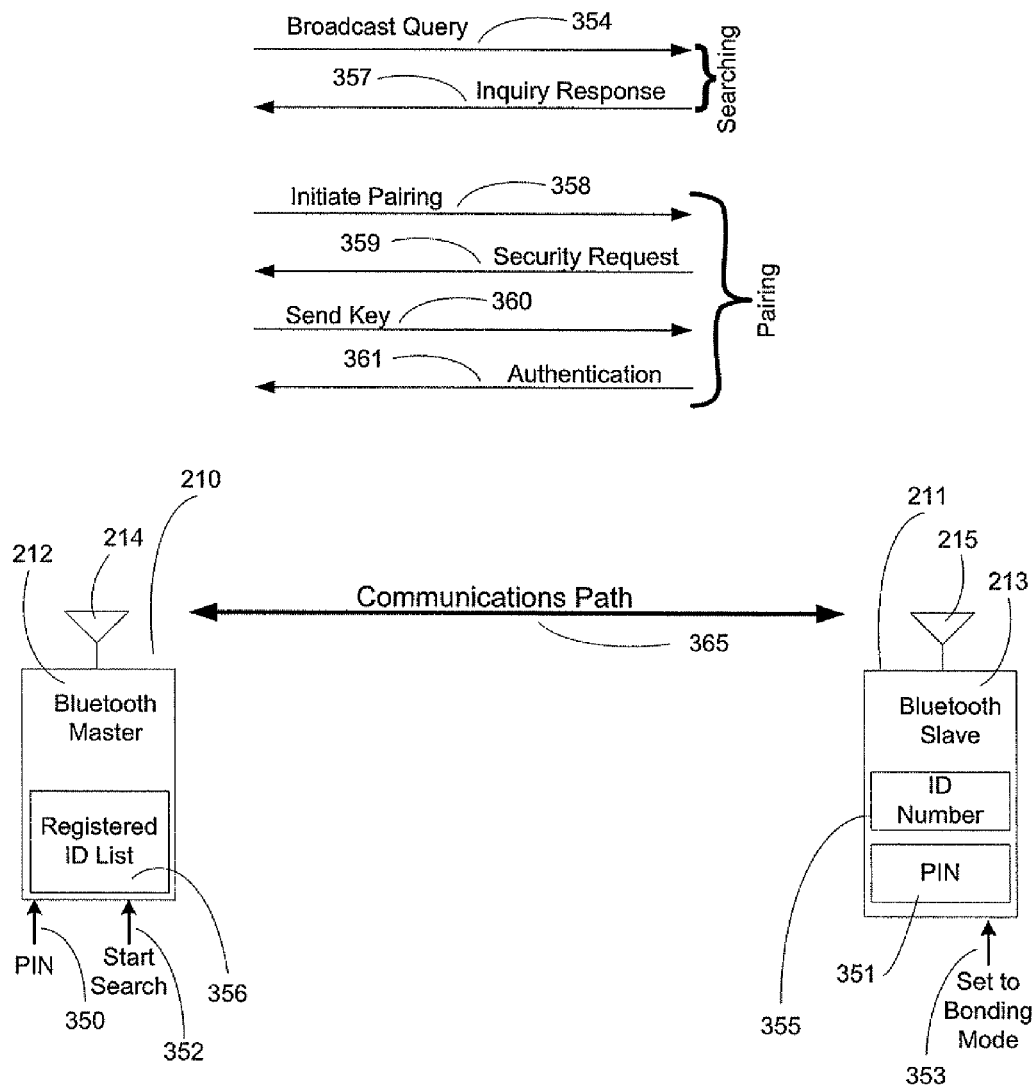
FIG. 3 illustrates the Bluetooth pairing mechanism sequence of events for searching and pairing master and slave Bluetooth enabled devices.

FIG. 3 illustrates the Bluetooth pairing mechanism between the Bluetooth master device 212 and the Bluetooth slave device 213. Before the pairing process can begin, a PIN code must be entered into both Bluetooth devices. Note that in some slave devices, for example wireless earphones, footpedal switches, and other peripheral devices, the PIN is fixed and cannot be changed. In such cases, the fixed PIN is entered into the Bluetooth master device 212. To start the pairing process, the Bluetooth slave device 213 must be set in the pairing mode. This is typically achieved by pressing a button on the wireless device 211 at 353. Pairing mode enables the Bluetooth slave device 213 to listen on antenna 215 for inquiry requests originating from the Bluetooth master device 212 as it transmits inquiry request on antenna 214 across the wireless communications network 230. Next, the fixed PIN 351 value stored within the Bluetooth slave device 213 is entered into controller 210. This is typically accomplished by the user entering the PIN 351 manually into the Bluetooth master device 212 at 350, or may be supplied electronically by an external system in the form of automatic provisioning at 350 (not shown).

At this point, the user may instruct the Bluetooth master device 212 to begin transmitting multiple inquiry requests to search for all available and in range Bluetooth slave devices 213. Typically the user selects "begin search mode" from a menu at 352 (not shown).

Beginning search mode causes a broadcast query 354 to be sent from the Bluetooth master device 212 to any in-range Bluetooth slave devices 213 for the purpose of discovering their Bluetooth slave addresses. Each Bluetooth slave device 213 that receives the broadcast query 354 follows a response procedure to return an inquiry response 357 to the Bluetooth master device 212. This response procedure includes the slave device providing its unique identification number 355 (i.e. slave address). The slave device may encapsulate its address in its inquiry response message. In parallel, the Bluetooth master device 212 listens for all inquiry responses 357 generated by the in range Bluetooth slave devices 213. The Bluetooth searching phase basically allows the master device to discover all available in range slave devices. The Bluetooth master device 212 compares each returned unique address to the Bluetooth slave addresses initially registered with and stored in the Bluetooth master device 212 at 356. When the Bluetooth master device 212 matches an address retuned from a slave device 213 to a registered identifier number, the Bluetooth searching phase is completed.

Next, the Bluetooth master device sends an initiate pairing 358 message to the registered slave device possessing the matching address. The slave device responds to the initiate pairing 358 request by sending a security request 359 as part of the pairing phase. The Bluetooth master device 212 responds to the security request 359 by generating a key based on the previously entered PIN number. The master device 212 sends this key at 360 to wireless device 211. If the Bluetooth master device 212 sends a valid key based on having the correct PIN number for the intended slave device, the Bluetooth slave device 213 returns an authentication 361 message. On successful authentication, the Bluetooth master and slave device form a communications path 365 and invokes encryption across this link based on the supplied key. Thus the pairing phase of the pairing process completes and the two devices are now able to send and receive data and information across this path.

Figure 4:
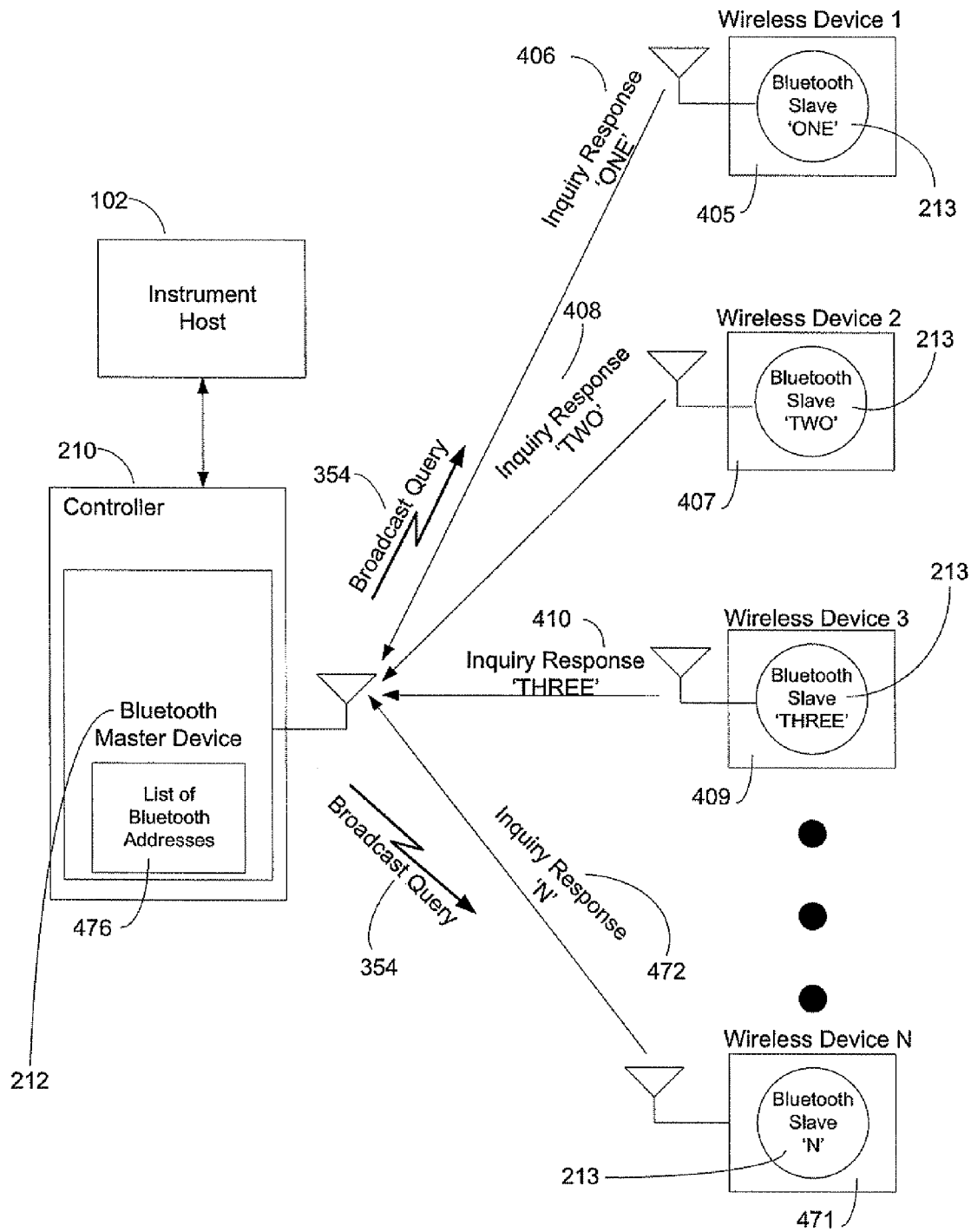
FIG. 4 illustrates the Bluetooth pairing mechanism in an environment where a plurality of Bluetooth slave devices are present and within broadcast query range.

FIG. 4 illustrates an exemplary wireless communication system employing a plurality of Bluetooth slave devices 213 and one Bluetooth master device 212. The Bluetooth master device 212 begins a device pairing process by sending a broadcast query 354 to all Bluetooth slave devices 213. The transmission of the broadcast query 354 from the Bluetooth master device 212 initiates a search for all Bluetooth slave devices 213 that are within reception range. The broadcast query 354 requests each Bluetooth slave device 213 to return its unique Bluetooth address 355.

For example, wireless device one at point 405 replies to the broadcast query 354 by sending an inquiry response 357 and provides its unique address 'ONE' at point 406 to Bluetooth master device 212. Wireless device two at point 407 replies to broadcast query 354 by sending an inquiry response 357 and provides its unique Bluetooth address 'TWO' at point 408. Wireless device three at point 409 replies to the broadcast query 354 by sending an inquiry response 357 and provides its unique Bluetooth address 'THREE' at point 410. In this example, all in-reception range wireless devices reply to the Bluetooth master device 212 broadcast requests 354. Wireless device 'N' at point 471 replies to the broadcast query 354 by sending an inquiry response 357 and provides its unique Bluetooth address 'N' at point 472. Bluetooth master device 212 creates and maintains a list of Bluetooth addresses at point 476 received from the queried wireless devices 405, 407, 409 and 471. The Bluetooth master device 212 compares the returned Bluetooth addresses to the address originally sent by the instrument host 102 or provided by the user. In this example, the instrument host 102 provided the Bluetooth master device 212 the unique address 'ONE' (not shown). The Bluetooth master device 212 searches the list of Bluetooth addresses 476 for a slave device that matches the previously registered unique address list stored at 356. In this example, the Bluetooth master device 212 matches with wireless device one at point 405 since it returned the desired unique address 'ONE'.

Bluetooth master device 212 then initiates a pairing process with wireless device 405. The Bluetooth master device 212 connects and communicates with only the Bluetooth slave device reporting the desired registered address and thus completes the pairing process. Once the pairing process concludes successfully, a wireless communications path 365 is established and becomes available for use between controller 210 implementing Bluetooth master device 212 and the intended wireless device one 405 implementing Bluetooth slave device 213 functionality.

After pairing with wireless device one at point 405, the Bluetooth master device may begin the pairing process for the remaining active Bluetooth slave devices 213 at point 407, 409, and 471. In this manner, the Bluetooth master device can successfully pair with one or more Bluetooth slave devices.

In an operating theater environment, safety issues may arise if the searching and pairing process acquires Bluetooth addresses from slave devices already in use. For example, if a non-fixed wireless medical subsystem device is required to perform a surgical task, the device must be first paired with an instrument host. When the instrument host initiates the pairing process for the non-fixed wireless medical device, the instrument host instructs the Bluetooth master device to search for all slave devices within range.

This may become problematic if the search includes slave devices that are within range and currently infuse in, for example, an adjacent operating room. Moreover, if the master device successfully pairs with a slave device in a different operating room, not only can this pose a safety hazard, but at a minimum will consume a great deal of time to eliminate this error. If a Bluetooth enabled slave device requires replacement during an operation, an efficient and reliable pairing process is paramount to continuing the procedure while minimizing disruption.

Exclusive Pairing Technique

Generally, the present design introduces a new connection establishment arrangement that modifies and enhances the current Bluetooth discovery and authentication mechanism offered with previous systems with a query response method between the controller 210 and the non-fixed wireless device 211 implementing Bluetooth slave device functionality. The present design may enable a Bluetooth connection to form and provide an exclusive communications path between a single master and a single slave device.

For simplicity, the present design system and method will be described for a Bluetooth communications path between the foot pedal subsystem and the instrument host subsystem that are part of a phacoemulsification machine, however the description may be applicable to any number of subsystems, for example the GUT host subsystem communicating with the instrument host subsystem, in communication with one another comprising part of or the entire medical system. In this configuration, the control and feedback of the phacoemulsification machine may be accomplished by exchanging data between the foot pedal subsystem and the instrument host. In this arrangement, the foot pedal subsystem may provide control signals to the instrument host, and the instrument host may provide control for the actual surgical devices connected to the instrument host.

Current wireless communication designs implementing the Bluetooth protocol provide a pairing mechanism enabling a Bluetooth master device to establish a communications path with one or more Bluetooth slave devices. Current designs enable the Bluetooth master device to discover one or more Bluetooth slave devices and authenticate with each slave device to form a communications path between a master and a slave device. The present design enables a Bluetooth master device to exclusively pair with a Bluetooth slave device. In this arrangement, the present design may allow a single master device to be paired with only one slave device at a time and not accept new pairing from additional slave devices until the first or initial device is explicitly unpaired.

The present design may modify the current Bluetooth communication path establishment mechanism on both the master and slave device to enable the master device to accept a single pairing with a slave device and write the master's unique device address into static memory, e.g. RAM, located on the slave device. When the master device desires to establish a connection with its paired slave device, the master may request that the slave device send the unique address stored locally in the slave, typically maintained in static memory. The master device may compare the address received from the slave device to its unique address. If a match condition is found, the master device may complete the connection and may establish a communication path with the slave device.

The present design ensures or guarantees that an exclusive communication path is established between the master and pre-selected or intended slave device.

Figure 5A:
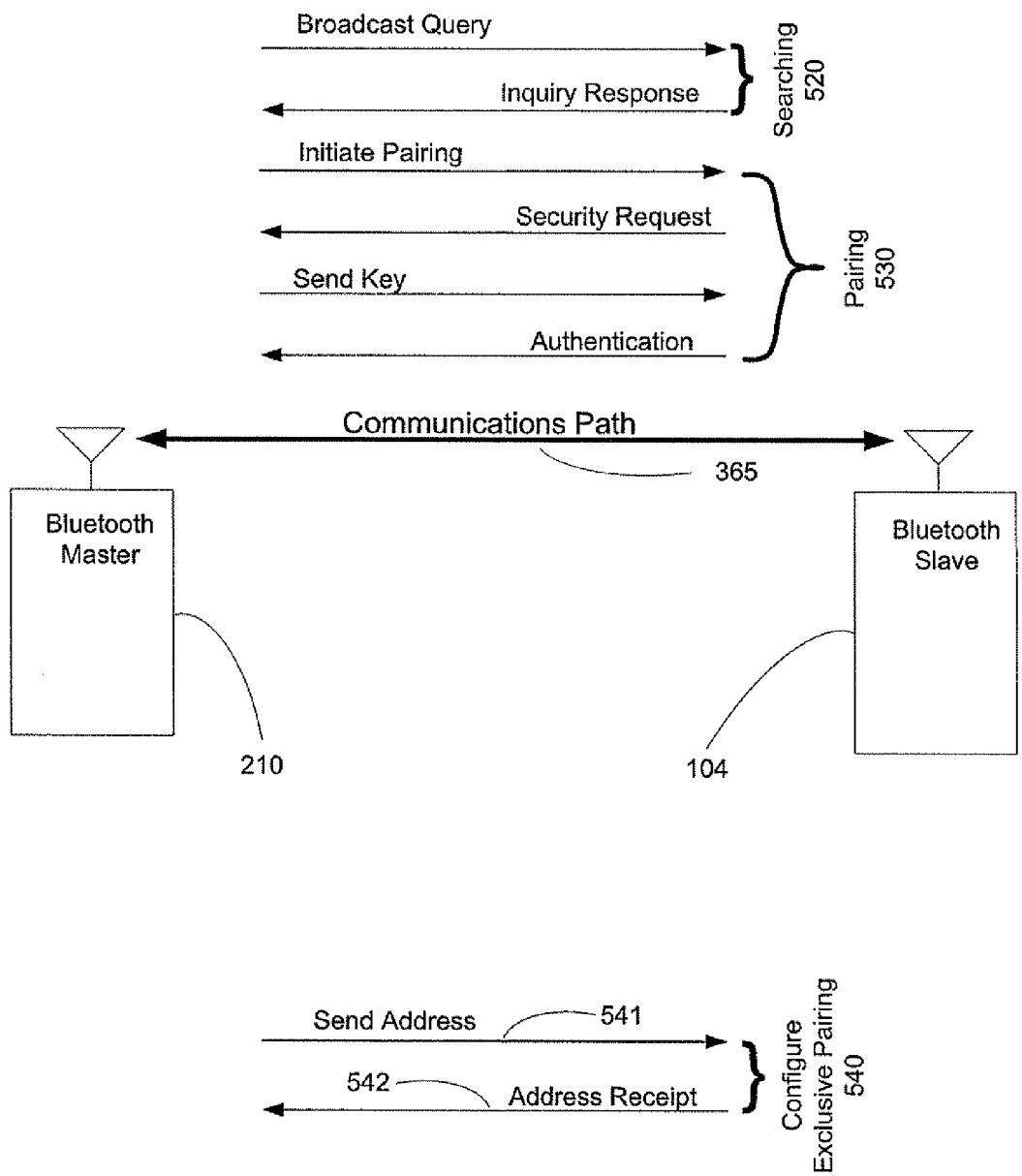
FIG. 5A illustrates the exclusive pairing configuration mechanism sequence of events for sending the Bluetooth master device address to a single Bluetooth enabled slave device.

FIG. 5A illustrates components and interfaces for configuring an exclusive master-slave communications relationship arranged between two Bluetooth enabled devices that may provide a single exclusive communications path between two wireless devices configured to establish a connection in accordance with the present design. Before the configuring process can begin, the present design may pair two wireless devices in accordance with the Bluetooth specification. For purposes of simplifying the example, this discussion assumes the appropriate PIN code(s) have been entered and each device is set in Bluetooth pairing mode such that the searching phase may begin as previously described. At this point, the user configuring wireless device 211 or another person ensures that only one wireless footpedal is currently within operating distance. For example, user may choose to configure wireless devices for exclusive pairing after office hours when no surgeries are being performed. The user may instruct the controller 210 to initiate the Bluetooth pairing process. The wireless controller 210 may establish a communications path 365 to wireless device 211 by executing the Bluetooth pairing process, including the searching 520 and pairing 530 phase, as previously described and in accordance with the Bluetooth specification. In the situation where at least one pre-selected wireless device 211 device is discovered, the present design then may complete the Bluetooth pairing process. Thus, the two wireless devices are able to send and receive data and information across communications path 365.

In the situation where one or more pre-selected wireless devices 211 or other undesirable Bluetooth enabled devices (not shown) are discovered, the present design may prevent more than one slave device from being configured at a time. The present design may configure exclusive pairing 540 for the first discovered pre-selected wireless device 211 where controller 210 may send a send address 541 message to the wireless device 211. The present design may write the received controller 210 address into static memory, such as static Random Access Memory (RAM), realized within the wireless device 211. The wireless device 211 may send an address receipt 542 message to controller 210 to indicate that the address was successfully stored to static memory. At this point, wireless device 211 has been configured to implement the exclusive pairing technique in accordance with the present design. The user may choose to configure additional pre-selected wireless devices 211 by repeating the above described exclusive pairing technique configuration process.

Figure 5B:
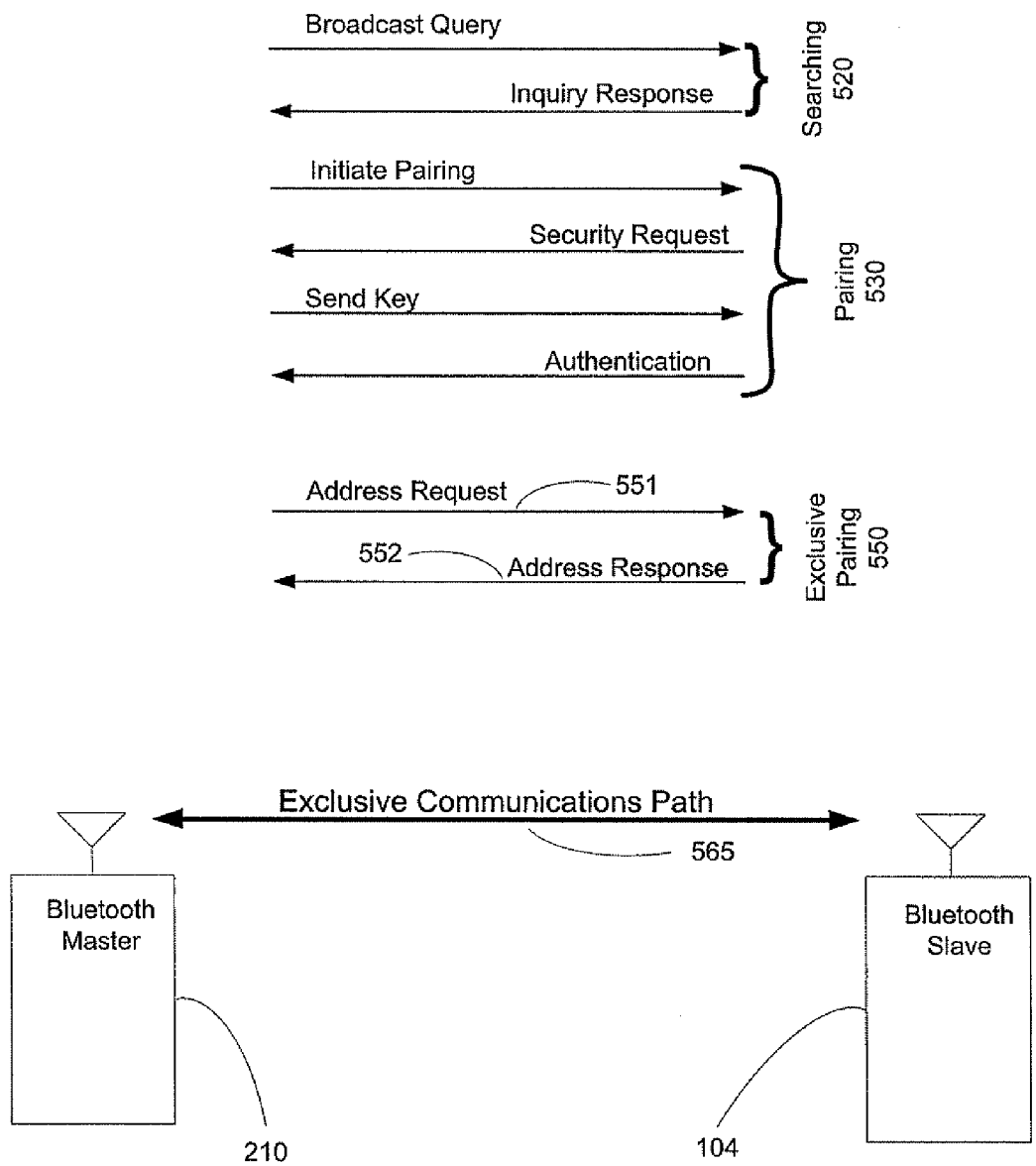
FIG. 5B illustrates the exclusive pairing operational mechanism sequence of events for retrieving the unique address stored in the Bluetooth slave device address and enabling an exclusive communications path in accordance with the present design.

FIG. 5B illustrates components and interfaces for operating an exclusive master-slave communications relationship arranged between two Bluetooth enabled wireless devices and may provide a single exclusive communications path between the two wireless devices previously configured to establish a connection in accordance with the present design. The user may instruct the controller 210 to initiate the Bluetooth pairing process. The wireless controller 210 may establish a communications path 565 to wireless device 211 by executing the Bluetooth pairing process, including the searching 520 phase and pairing 530 phase, and executing the present design exclusive pairing 550 technique. The present design may realize the exclusive pairing 550 technique where controller 210 sends an address request 551 message to wireless device 211. The wireless device 211 may receive this message and may read the previously stored controller address from static memory and return this address by sending an address response 552 message to the controller that originated the above described exclusive pairing sequence.

Controller 210 may compare the address obtained from the wireless device 211 address response 552 message to its unique address. If the returned address is found to match the controller's unique address, the present design may form an exclusive communications path 565 between controller 210 and wireless device 211 realized by implementing the exclusive pairing 550 technique in accordance with the present design. If the returned address does not match the controller's unique address, the present design may explicitly "un-pair" the two wireless Bluetooth devices and close any existing connections to end any communications between controller 210 and wireless device 211.

Figure 6A:
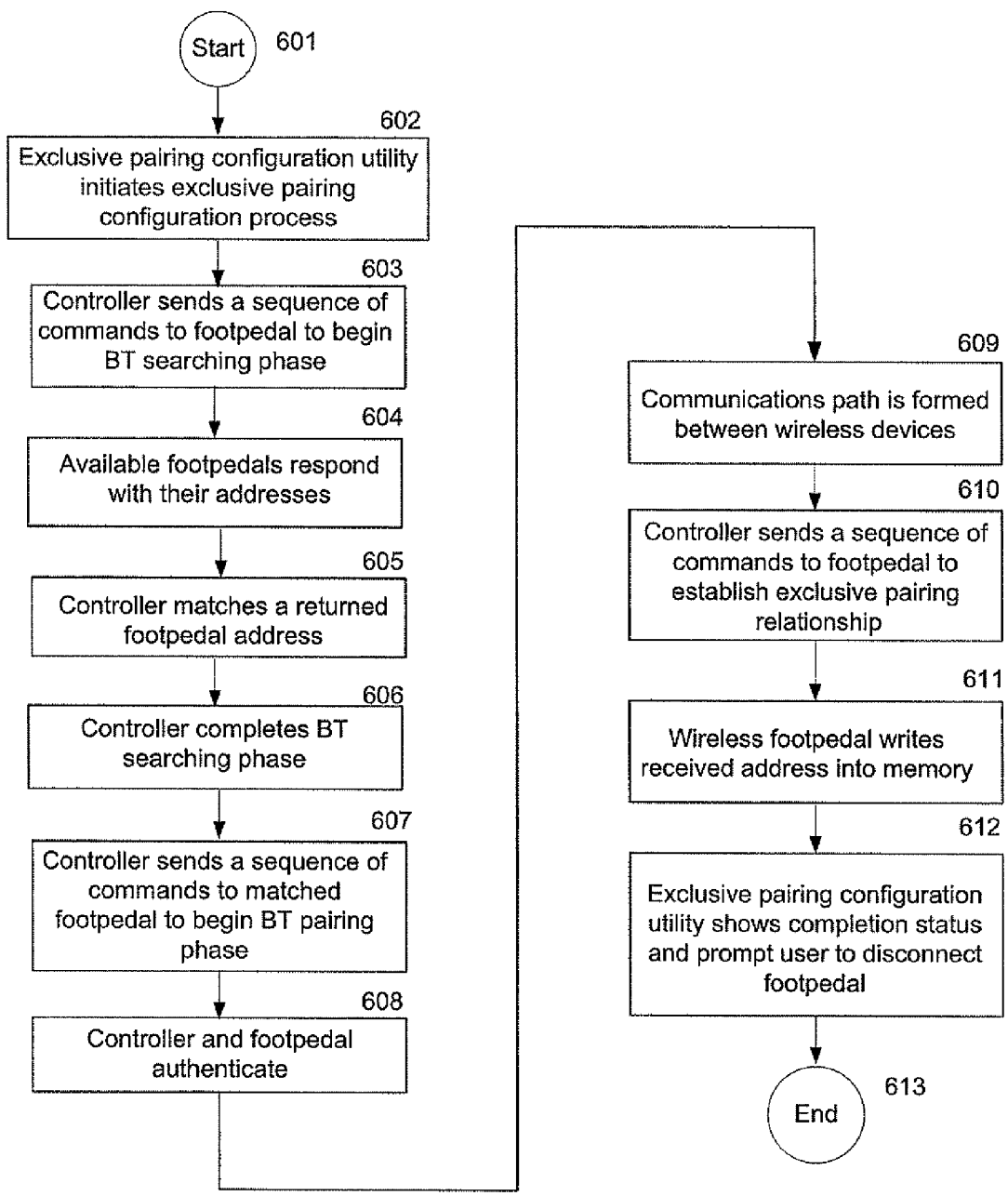
FIG. 6A is a flowchart representing the general operation of the system in configuration mode in accordance with the present design.

FIG. 6A illustrates general operation of the system in a configuration mode. From FIG. 6A, point 601 establishes start of the configuration mode arrangement for the exclusive pairing 550 technique in accordance with the present design. The GUI host 101, instrument host 102, or controller 210 may start an exclusive pairing configuration utility at 602 to initiate the configuration process in accordance with the present design. Once initiated, the controller 210 may send a sequence of commands at 603 to wireless footpedal 104 switch subsystem to begin the searching phase. Wireless footpedals within signal reach and set in Bluetooth pairing mode respond with their addresses. Controller 210 may match a responding wireless footpedal 104 switch subsystem address at 605 in accordance with the Bluetooth specification and complete the searching 520 phase at 606. As part of the normal Bluetooth pairing process, controller 210 may send a sequence of commands to the previously matched wireless footpedal 104 switch subsystem to begin the Bluetooth pairing 530 phase. At point 608, the controller 210 and wireless footpedal 104 switch subsystem may authenticate and complete the Bluetooth pairing process.

At this point a communications path is formed at 609 between controller 210 and wireless footpedal 104 switch subsystem. Controller 210 may send a sequence of commands at 610 to wireless footpedal 104 switch subsystem to establish the exclusive pairing mechanism. The controller may send its unique address to the wireless footpedal, and the wireless footpedal may write this received address into local static memory at 611. Wireless footpedal 104 switch subsystem may send an address response message to controller 210 to indicate that their address has been successfully stored and available for retrieval. The present design may forward a message based on the address response message to the exclusive pairing configuration utility and may enable completion status to be indicated or displayed. The exclusive pairing configuration utility may include a graphical user interface for display of status information and input controls. At this point the exclusive pairing configuration utility may prompt the user to disconnect the footpedal. In addition, the present design may include an option to allow the user to establish an exclusive communications path between the controller and wireless footpedal in lieu of disconnecting the wireless footpedal.

Figure 6B:
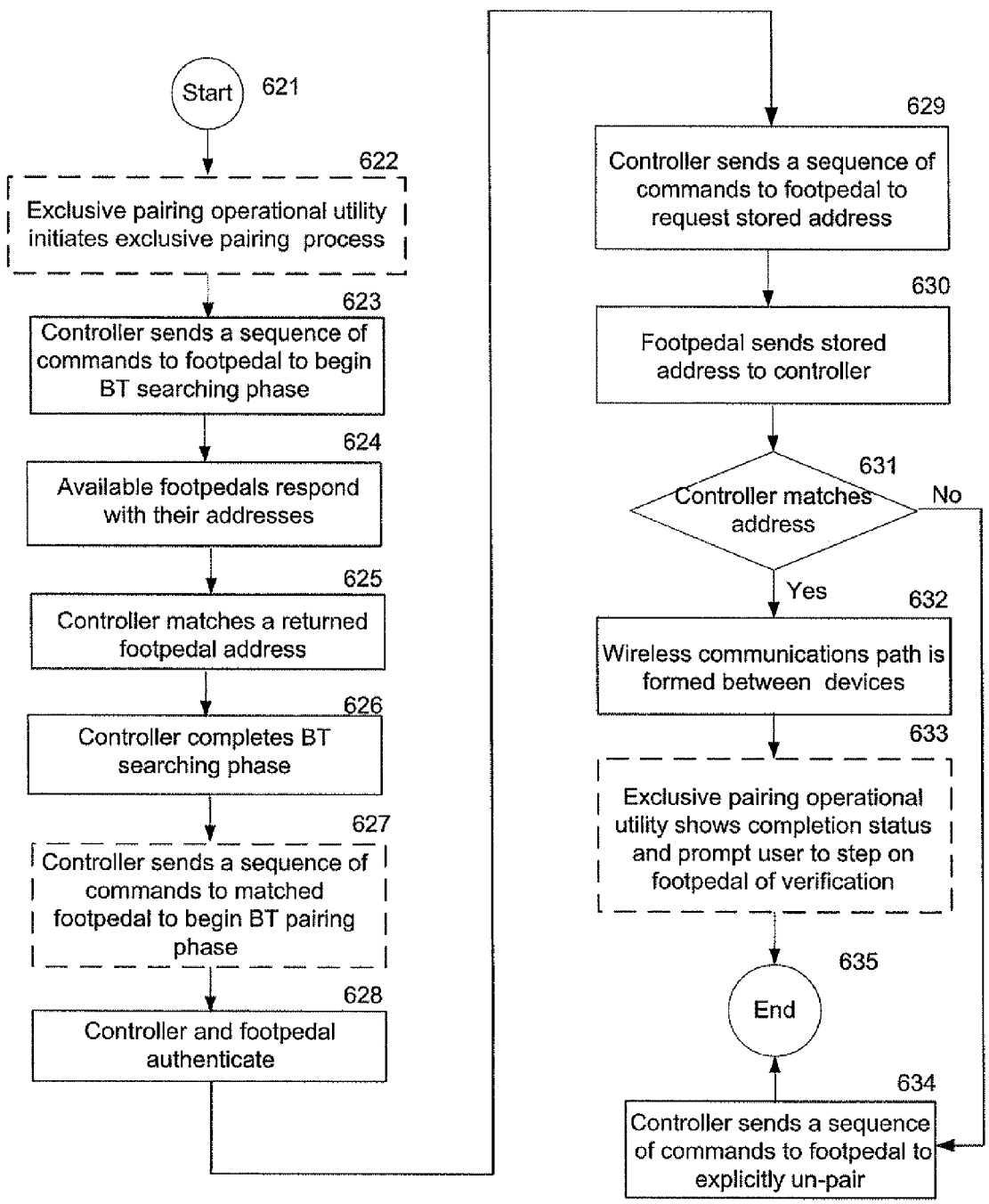
FIG. 6B is a flowchart representing the general operation of the system in operational mode in accordance with the present design.

FIG. 6B illustrates general operation of the system. From FIG. 6B, point 621 establishes the start of the exclusive pairing 550 technique in accordance with the present design. The GUI host 101, instrument host 102, or controller 210 may start an exclusive pairing operations utility at 622 to initiate the exclusive pairing process in accordance with the present design. Once initiated, the controller 210 may send a sequence of commands at 623 to wireless footpedal 104 switch subsystem to begin the searching 520 phase. Wireless footpedals within signal reach that are set in Bluetooth pairing mode respond with their addresses at 624. Controller 210 may match a responding wireless footpedal 104 switch subsystem address at 625 in accordance with the Bluetooth specification and complete the searching 520 phase at 626. As part of the normal Bluetooth pairing process, controller 210 may send a sequence of commands to the previously matched wireless footpedal 104 switch subsystem to begin the Bluetooth pairing 530 phase at 627. At point 628, the controller 210 and wireless footpedal 104 switch subsystem may authenticate and complete the Bluetooth authentication process. At this point, controller 210 may send a sequence of commands to the matched wireless footpedal 104 switch subsystem to request the stored unique address at point 629. Wireless footpedal 104 switch subsystem may send the stored address to controller 210 at point 630. The controller may compare the address returned from the wireless footpedal 104 switch subsystem to its unique address at point 631. If a match condition is found to exist, the present design may form an exclusive communications path 565 between the controller and wireless footpedal at point 632.

Once the controller 210 and wireless footpedal 104 switch subsystem successfully establish an exclusive connection, controller 210 may report to instrument host 102 that the exclusive communication path 565 between the two wireless devices has been established. At point 633, the exclusive pairing operational utility may show a completion status to the user and may prompt the user to step on the wireless footpedal to verify operation. The exclusive pairing operational utility may include a graphical user interface for display of status information and input controls. When the communications path 565 is verified, the process ends at point 635 and the devices are ready for use.

In the situation where a match is not found, the present design may send a sequence of commands to the wireless footpedal 104 switch subsystem instructing it to implicitly un-pair at 634 to close any existing Bluetooth connections and end the exclusive pairing process at point 635.

FIG. 6B illustrates three modules in the flowchart that may be considered optional components, each highlighted with a dashed line. These components (622, 627, and 633) may or may not be employed as desired due to the nature of Bluetooth pairing.

Although the configuration utility and operational utility are described separately, the two exclusive pairing utilities may be realized in one or more subsystems or modules.

Wireless Footpedal

Figure 7:
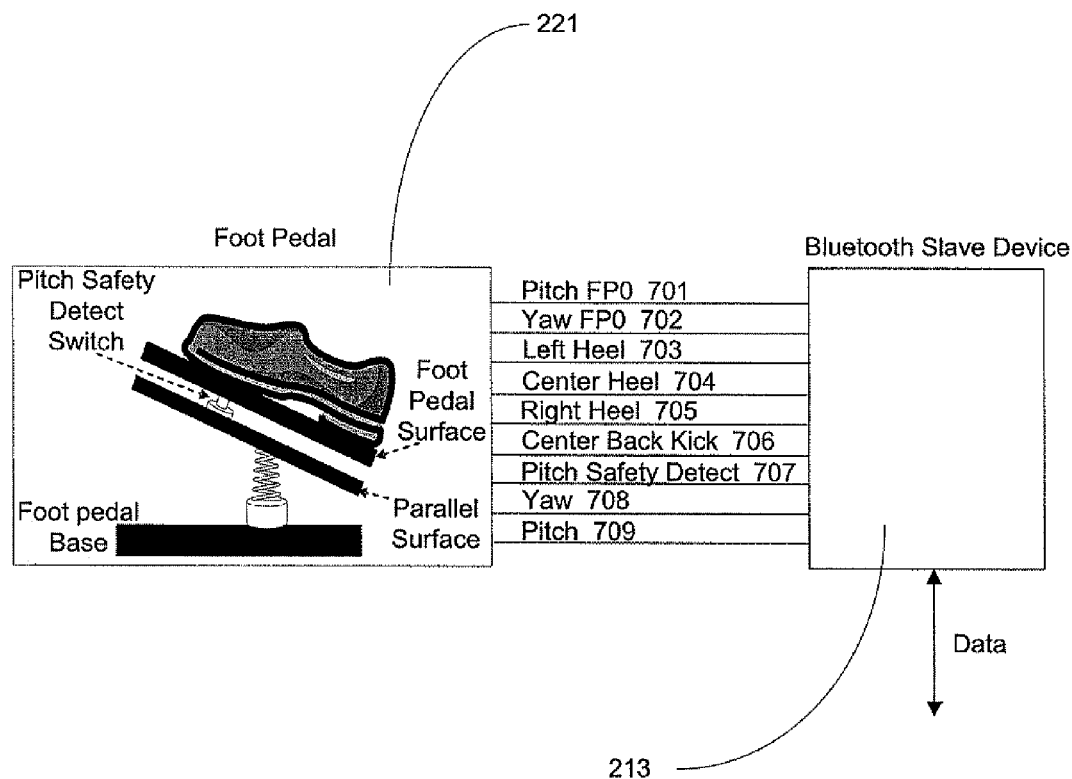
FIG. 7 illustrates a footpedal that may be employed in accordance with the current design.

FIG. 7 illustrates a switch subsystem for wireless foot pedal 104 that may be employed in accordance with the current design. In the embodiment illustrated, the Bluetooth slave device 213 receives one or more control signals from footpedal 221. The control signals generated by the footpedal 221 may report the status of various physical and virtual switches contained within or other parameters such as yaw linear position and vertical linear position. The footpedal firmware within the footpedal 221 reads and processes the switch inputs. The footpedal 221 produces a data stream representing control signals resulting from the button and switch positions triggered on the footpedal 221. The control signals are ultimately destined for the instrument host 102. Control signals may include but are not limited to position of a footpedal, such as left heel 703, center heel 704, right heel 705, pitch safety detect 706, pitch 707, and yaw 708 positions; button pushes or "stomp" values, or other appropriate states in the case of a footpedal. Moreover, predefined footpedal positions FP0, FP1, FP2, or FP3 (FPn) may be communicated. For example, pitch FP0 701 and yaw FP0 702 may be communicated when the footpedal 221 is connected.

Figure 8:
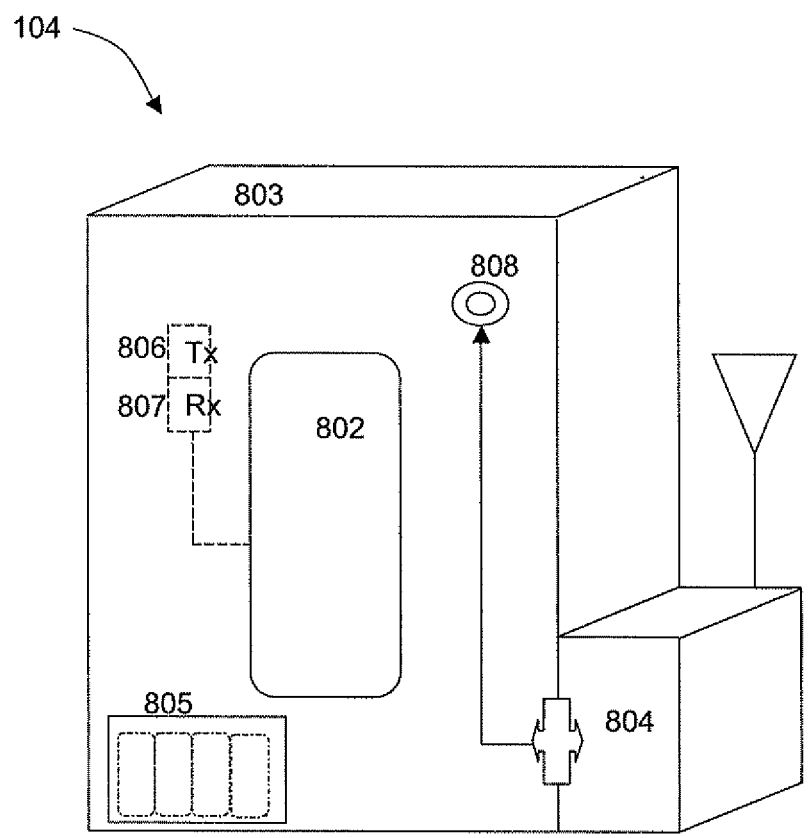
FIG. 8 shows the conceptual connections between the footpedal and the base unit and power source.

FIG. 8 shows the conceptual connections between the footpedal 221 and the base unit and power source. Footpedal 221 includes pedal 802, base 803, and communications interface 804 here shown at the side of the base 803. The footpedal 221 in this view includes batteries 805, typically rechargeable batteries. A transmitter 806 and receiver 807 are provided in the footpedal 221 in this embodiment and connect to the communications interface 804 to access the antenna 215, and in this embodiment a "connection LED" 808 is provided that is constantly on when the wireless device 211 data channel is available for operational use. When a data channel becomes disconnected due to interference or other causes, the connection LED 808 may blink on and off, warning the user that the data channel is lost or disconnected and communication redundancy is not available. Blinking in this manner enables the surgeon to decide whether to continue the procedure or obtain a new wireless device 211. Other notification methods may be employed, including but not limited to optical (e.g. one LED per channel) and audio notification methods.

The present designs exclusive master-slave data communications relationship may alternatively be used between any two modules that are communicating via any asynchronous media. This communications protocol may be realized in either hardware or software. In addition, this communications protocol may be implemented inside another protocol, including but not limited to, Bluetooth and Transmission Control Protocol/Internet Protocol.

The foregoing is not determinative or exclusive or inclusive of all components, interfaces, communications, and operational modes employable within the present design. The description of specific embodiments reveals the general nature of the disclosure sufficiently that others can, by applying current knowledge, readily modify and/or adapt the system and method for various applications without departing from the general concept. The design presented herein and the specific aspects illustrated are meant not to be limiting, but may include alternate components while still incorporating the teachings and benefits of the invention, namely a wireless exclusive master-slave data communications management apparatus employing a wireless medical device, wireless controller, a communications network, and instrument host system to facilitate surgeons while performing procedures. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains. Therefore, such adaptations and modifications are within the meaning and range of equivalents of the disclosed embodiments. The phraseology or terminology employed herein is for the purpose of description and not of limitation.

What is claimed is:

1. A method for exclusively pairing wireless devices in a medical environment, comprising:
    providing a Bluetooth connection between at least two wireless devices, wherein a master wireless device is configured with Bluetooth master device functionality and a slave wireless device is configured with Bluetooth slave device functionality, wherein the master wireless device comprises a master wireless medical device and the slave wireless device comprises a slave wireless medical device, and wherein the slave wireless device is configured to control a surgical instrument host via the master wireless device;
    providing a master personal identification number of the master wireless device to the slave wireless device and at least one slave personal identification number of at least one slave wireless device to the master wireless device;
    acquiring, at the master wireless device, one unique slave address from one slave wireless device;
    comparing, at the master wireless device, the unique slave address to a listing of slave wireless device unique addresses available at the master wireless device to determine at least one candidate slave wireless device;
    generating, at the master wireless device, a key based on the slave personal identification number of one candidate slave wireless device;
    transmitting the key from the master wireless device to the one candidate slave wireless device; and
    exclusively pairing the master wireless device and the one candidate slave wireless device when the key acquired from the master wireless device matches one wireless unique address in the listing of slave wireless device unique addresses, and the one candidate slave wireless device provides an authentication message to the master wireless device.

2. The method of claim 1, wherein exclusively pairing enables a master-slave communications path to connect one master wireless device to one slave wireless device.

3. The method of claim 1, wherein the master wireless device further establishes a single exclusive pairing with one slave wireless device at one time.

4. The method of claim 1, further comprising:
    retrieving a master wireless device unique address from the slave wireless device; and
    sending the master wireless device unique address from the one slave wireless device to the master wireless device when requested by the master wireless device.

5. The method of claim 1, wherein the comparing further comprises determining whether one from a plurality of received slave addresses for exclusive pairing matches more than one wireless unique address in the listing of slave wireless device unique addresses.

6. The method of claim 1, further comprising explicitly un-pairing one master wireless device and one slave wireless device when the acquired stored unique slave address does not match one from a plurality of received slave addresses.

7. An exclusive pairing medical system for pairing a Bluetooth compliant medical slave device to a medical surgical instrument host comprising a Bluetooth pairing utility and an exclusive pairing utility, the exclusive pairing medical system comprising;
    a medical device controller configured to control communications between the surgical instrument host and the Bluetooth compliant medical slave device over a wireless communications network and enable exclusive pairing between the surgical instrument host and the Bluetooth compliant medical slave device;
    wherein the device controller is configured to receive an address from the surgical instrument host, and wherein the device controller is configured to receive at least one slave personal identification number of at least one Bluetooth compliant medical slave device and generate and transmit a key based on the slave personal identification number of one candidate Bluetooth compliant medical slave device;
    wherein the surgical instrument host is configured to establish exclusive pairing between the surgical instrument host and one Bluetooth compliant medical slave device over the wireless communications network when a slave device unique address of the Bluetooth compliant medical slave device matches one slave device unique address maintained by the surgical instrument host, the key transmitted from the surgical instrument host corresponds to the slave personal identification number of the one candidate Bluetooth compliant medical slave device, and the one candidate Bluetooth compliant medical slave device provides an authentication message to the surgical instrument host; and
    wherein the Bluetooth compliant medical slave device is configured to control the surgical instrument host via the medical device controller.

8. The system of claim 7, wherein the Bluetooth compliant medical slave device comprises a foot pedal switch.

9. The system of claim 7, wherein the Bluetooth pairing utility comprises a graphical user interface for managing Bluetooth device discovery and authentication.

10. The system of claim 9, wherein the exclusive pairing utility further comprises a graphical user interface for managing the configuration and operation of exclusively connected non-fixed slave devices.

11. The system of claim 7, wherein the medical device controller comprises master device functionality capable of transmitting information to and receiving information from the Bluetooth compliant medical slave device.

12. The system of claim 7, wherein the Bluetooth compliant medical slave device includes Bluetooth slave device functionality capable of transmitting information to and receiving information from the medical device controller.

13. The system of claim 7, wherein the medical instrument host and medical device controller are configured to exclusively pair the medical instrument host to a plurality of medical slave devices having Bluetooth functionality.

14. A method for providing exclusive Bluetooth communication between a controller and a medical device, comprising:
    establishing a Bluetooth communications path between the controller and the medical device;
    providing a master personal identification number of the controller to the medical device and at least one medical device personal identification number of at least one medical device to the controller;
    wirelessly providing a controller unique address from the controller to the medical device;
    storing the controller unique address at the medical device; and acquiring, at the controller, one stored unique address from one medical device;

comparing, at the controller, the one stored unique address to a listing of medical device unique addresses available at the controller to determine at least one candidate slave device;

generating, at the controller, a key based on the personal identification number of one candidate medical device;

transmitting the key from the controller to the one candidate medical device;

forming an exclusive communications path between the controller and only the one medical device using a unique address obtained from the medical device by the controller when the key acquired from the controller corresponds to the personal identification number of the one candidate medical device, wherein the one candidate medical device provides an authentication message to the controller; and controlling, by the medical device, a surgical instrument host via the controller.

15. The method of claim 14, wherein the Bluetooth communications path is formed in accordance with a Bluetooth discovery and authentication specification.

16. The method of claim 14, wherein the forming further comprises sending the unique address from the medical device over a wireless network in response to queries from the controller.

17. The method of claim 14, wherein forming the exclusive communications path further comprises selecting one from a plurality of candidate medical devices for exclusive pairing when more than one unique address matches addresses in the list of addresses maintained at the controller.

18. The method of claim 14, wherein the exclusive communications path is formed when the unique address acquired from the medical device is found by the controller to be an identical match with one unique address in the list of addresses maintained at the controller.

19. The method of claim 14, further comprising explicitly un-pairing medical device from the controller when the unique address acquired from the medical device is found by the controller to not match any address in the list of addresses maintained at the controller.

20. The method of claim 14, wherein pairing devices enables a master-slave communications path to connect a single master device to a single slave device.

21. The method of claim 14, wherein the controller further establishes a single exclusive pairing with a single medical device at any one time.

* * * * *